US010428454B2

(12) United States Patent
Nikam et al.

(10) Patent No.: US 10,428,454 B2
(45) Date of Patent: Oct. 1, 2019

(54) TEXTILE TREATMENT COMPOSITIONS INCLUDING QUTERNARY BIS-IMIDAZOLINE COMPOUNDS DERIVED FROM LINEAR TETRAMINES USEFUL TO IMPROVE MOISTURE MANAGEMENT AND PROVIDE ANTIMICROBIAL PROTECTION

(71) Applicant: Dow Global Technologies LLC, Midland, MI (US)

(72) Inventors: Sandeep Nikam, Vikhroli (IN); Ritesh Gulabani, Vadodara (IN); Yogaraj Nabar, Vikhroli (IN); Prashant Tatake, Hyderabad (IN)

(73) Assignee: Dow Global Technologies LLC, Midland, MI (US)

( * ) Notice: Subject to any disclaimer, the term of this patent is extended or adjusted under 35 U.S.C. 154(b) by 291 days.

(21) Appl. No.: 15/107,773

(22) PCT Filed: Dec. 12, 2014

(86) PCT No.: PCT/US2014/069936
§ 371 (c)(1),
(2) Date: Jun. 23, 2016

(87) PCT Pub. No.: WO2015/100032
PCT Pub. Date: Jul. 2, 2015

(65) Prior Publication Data
US 2016/0319479 A1    Nov. 3, 2016

(30) Foreign Application Priority Data

Dec. 27, 2013  (IN) .......................... 6134/CHE/2013

(51) Int. Cl.
| *D06M 13/473* | (2006.01) |
| *A01N 33/12* | (2006.01) |
| *D06M 13/467* | (2006.01) |
| *A01N 43/50* | (2006.01) |
| *C07D 233/16* | (2006.01) |
| *D06M 16/00* | (2006.01) |
| *C07D 233/06* | (2006.01) |

(52) U.S. Cl.
CPC .......... *D06M 13/473* (2013.01); *A01N 33/12* (2013.01); *A01N 43/50* (2013.01); *C07D 233/06* (2013.01); *C07D 233/16* (2013.01); *D06M 13/467* (2013.01); *D06M 16/00* (2013.01)

(58) Field of Classification Search
None
See application file for complete search history.

(56) References Cited

U.S. PATENT DOCUMENTS

| 2,194,419 A | 3/1940 | Chwala |
| 2,918,474 A | 12/1959 | Hughes |
| 3,887,476 A | 6/1975 | McConnell |
| 4,458,080 A | 7/1984 | Boehmke et al. |
| 4,601,911 A | 7/1986 | Ueno et al. |
| 4,614,600 A | 9/1986 | Schilling et al. |
| 4,713,184 A | 12/1987 | Zaid |
| 5,611,992 A | 3/1997 | Naraghi et al. |
| 5,643,498 A | 7/1997 | Li et al. |
| 8,187,997 B2 | 5/2012 | King et al. |
| 8,188,318 B2 | 5/2012 | Petraitis et al. |
| 8,293,676 B2 | 10/2012 | King et al. |
| 2002/0160926 A1 | 10/2002 | Trinh et al. |
| 2010/0094007 A1 | 4/2010 | King et al. |
| 2013/0090453 A1 | 4/2013 | Luyken et al. |
| 2013/0204044 A1 | 8/2013 | Mehta et al. |

FOREIGN PATENT DOCUMENTS

| CN | 1584121 A | 2/2005 |
| CN | 101565608 A | 10/2009 |
| DE | 3135235 A1 | 3/1983 |
| JP | H6268356 A | 9/1994 |
| JP | 9241636 A | 9/1997 |
| JP | 2000096272 A | 4/2000 |
| MX | PA03011620 A | 6/2005 |
| MX | PA03011659 A | 6/2005 |
| RU | 2357007 C2 | 5/2009 |
| WO | 92/22535 A1 | 12/1992 |
| WO | 98/42898 A1 | 10/1998 |
| WO | 98/49898 A1 | 11/1998 |
| WO | 00/28131 A2 | 5/2000 |
| WO | 0049204 A1 | 8/2000 |
| WO | 2009088702 A1 | 7/2009 |

OTHER PUBLICATIONS

Shin, et al. (1996) "A New Synthetic Route to Poly(benzimidazole) and the Related Model Reactions to Imidazoline and Benzimidazole", Bull. Korean Chem. Soc., 17(1):29-33.
Braddok, et al. (2010) "The reaction of aromatic dialdehydes with enantiopure 1,2-diamines: an expeditious route to enantiopure tricyclic amidines", Tetrahedron: Asymmetry, 21:2911-2919.
Demadis, et al. (2007) "Degradation of Phosphonate-Based Scale Inhibitor Additives in the Presence of Oxidizing Biocides: "Collateral Damages" in Industrial Water Systems", Separation Science and Technology, 42:1639-1649.
Zhao, et al. "The synergistic inhibition effect of oleic based imidazoline and sodium benzoate on mild steel corrosion in a CO2 saturated brine solution", Electrochimica Acta 69, 2012, pp. 247-255.
Farelas et al., "Carbon Dioxide Corrosion Inhibition of Carbon Steels Through Bis-imidazoline and Imidazoline Compounds Studied by EIS", International Journal of Electrochemical Science, 5 (2010) 797-814.

(Continued)

*Primary Examiner* — Kamal A Saeed
(74) *Attorney, Agent, or Firm* — Kagan Binder, PLLC

(57) ABSTRACT

The present invention provides strategies to improve the moisture management properties of textiles while retaining high comfort levels. The treatments also help to protect textiles against microbial growth. The treatment strategies of the present invention are based at least in part on the use of cationic bis-imidazoline(s) and their salts. Quaternized bis-imidazoline cations and their salts are particularly preferred.

8 Claims, 1 Drawing Sheet

(56) References Cited

OTHER PUBLICATIONS

Huang, H., (2003) "Overview of Surfactants in China", Chemical Industry Press, pp. 1-6 (translation).

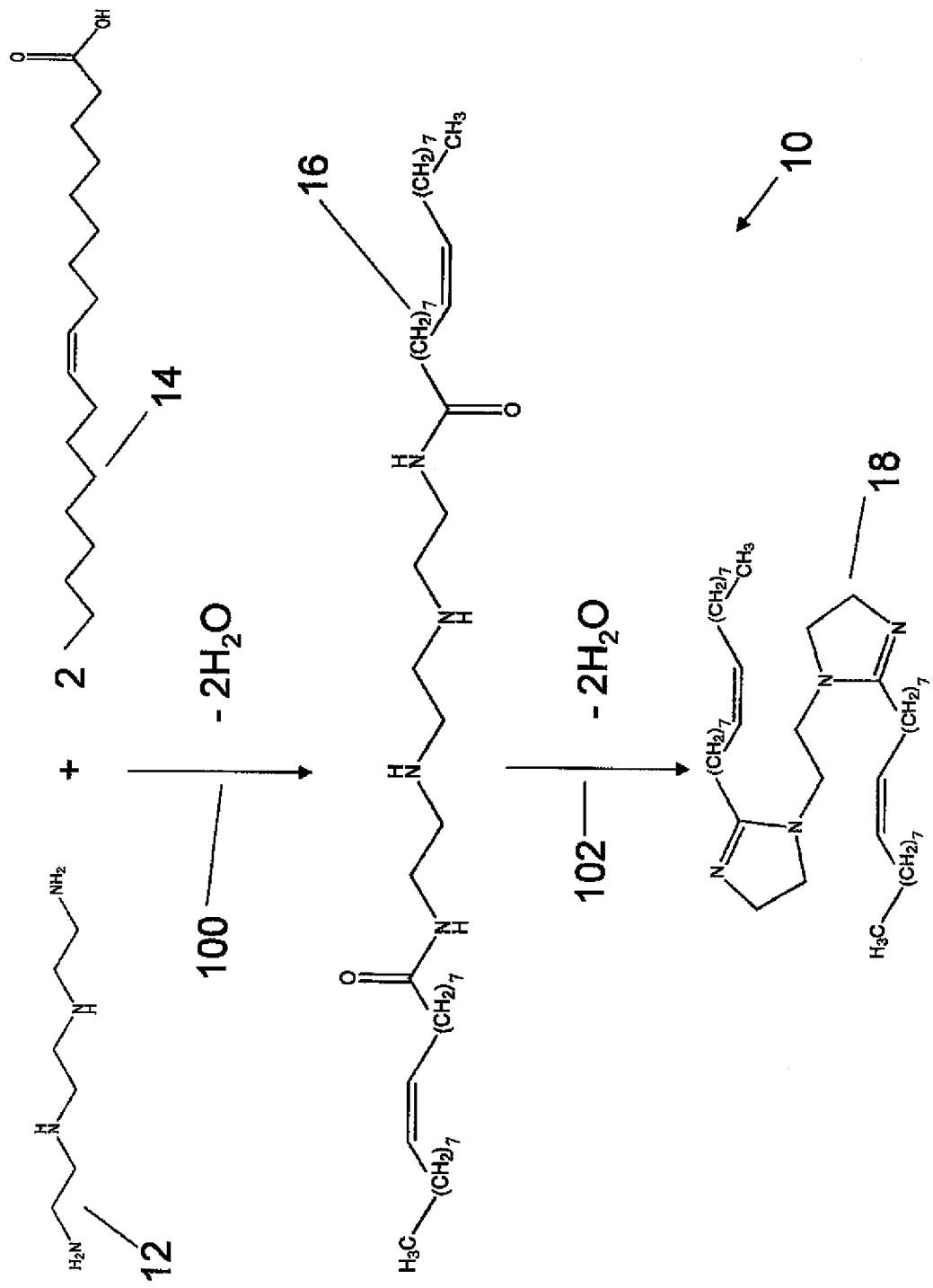

TEXTILE TREATMENT COMPOSITIONS INCLUDING QUTERNARY BIS-IMIDAZOLINE COMPOUNDS DERIVED FROM LINEAR TETRAMINES USEFUL TO IMPROVE MOISTURE MANAGEMENT AND PROVIDE ANTIMICROBIAL PROTECTION

CROSS-REFERENCE TO RELATED APPLICATIONS

This application claims priority to International Application No. PCT/US2014/069936, filed Dec. 12, 2014, which in turn claims priority to Indian Patent Application No. 6134/CHE/2013, filed Dec. 27, 2013, wherein the disclosures of these applications are incorporated herein by reference in their respective entireties for all purposes.

FIELD OF THE INVENTION

The present invention relates to textile treatment compositions and their use to help improve moisture management and to help provide antimicrobial protection in textiles incorporating natural and/or synthetic materials, wherein the compositions comprise one or more bis-imidazoline cations and/or salts thereof that are functionalized with hydrophobic moieties on both imidazoline rings of the bis-imidazolines. More particularly, the present invention relates to such treatment compositions and their use in which a tetramine admixture comprising one or more linear tetramines is used to prepare the bis-imidazoline material(s).

BACKGROUND OF THE INVENTION

A textile is a material comprising a network of synthetic and/or natural fibers. The fibers may be referred to as thread or yarn in some applications. Often, textiles are provided in the form of woven or nonwoven, flexible fabrics or cloth. In some applications, such as a carpet, the textile includes fibers attached to a suitable backing.

Textiles can be formed from a wide range of materials. Materials used to make textiles can be sourced from animals, plants, minerals, and/or synthetic materials. Examples of such materials include hair, fur, skin, silk, grass, rush, hemp, sisal, straw, hay, bamboo, pulpwood, cotton, rice, nettle, flax, jute, modal, pina, seaweed, basalt, glass fiber, metal fiber and foil, polyester, polyaramid, acrylic, polyamide, polyimide, polyurethane, polyolefin, polyacrylonitrile, rubber, carbon, protein, combinations of these, and the like.

Textile materials can be used to form a large range of finished articles. These include, for example, leather articles, rugs, carpets, fabrics, liners, thread, garments, tarps, bags, baskets, luggage, medical coverings, bedding, towels, art surfaces, wall coverings, flags, tents, handkerchiefs, balloons, kites, sails, parachutes, brushes, mattresses, sacks, hammocks, awnings, and the like.

Moisture management in the context of textile applications, such as for clothing items, relates to a textile's ability to effectively transport moisture (perspiration) away from the underlying substrate, e.g., skin surface, to the external atmosphere (including, e.g., absorption from skin, passage through the fabric by capillary or other action, and evaporation or other transport away from the surface). In hot conditions, trapped moisture may heat up and lead to fatigue or diminished performance. In cold conditions, trapped moisture may drop in temperature and cause chilling and hypothermia. Excess moisture may also cause a garment to become heavy, as well as cause damage to the skin from chafing. All these effects are more pronounced in the case of synthetic fabrics like polyester and its blended forms. Efficient moisture management is important to maintain the comfort level of a fabric under different weather conditions. Moisture management is of particular concern in applications involving sportswear, premium innerwear, and other performance apparel.

Another issue that occurs when textiles are exposed to moisture is the potential for microbial growth. The risk of microbial growth is increased when moisture is trapped and cannot escape to the ambient.

Moisture management is a concern for both natural and synthetic fibers. Synthetic fibers generally are much less hydrophilic than natural fibers. Moisture management is more challenging, therefore, when a textile is made wholly or in part from synthetic, hydrophobic fibers.

Many attempts have been proposed and practiced in the prior art to address these problems. One strategy involves increasing the hydrophilicity of the textile so that moisture can escape, and the textile can dry in a reasonable time. For example, the problem of poor water absorption of synthetic fibers can be mitigated by the mixed spinning or mixed weaving with more hydrophilic natural fibers. The effectiveness of this method is limited. If too much natural fiber is combined with the synthetic fibers to attain sufficient hydrophilicity, the advantages provided by synthetic fibers may be diluted too much.

An alternative strategy involves treating textiles with compositions including one or more additives that improve moisture management and/or antimicrobial properties. Some of these treatments can be effective, but only for a short time. Improved performance may occur when a fabric is new, but the treatments can lose substantial efficacy quite quickly after a textile is washed or used. Some treatments might only be effective at high concentration. This can alter the hand or comfort of a garment, making the treated fabric less appealing to consumers.

Although substantial work has been done in the textile field to address moisture management and antimicrobial protection, there remains a strong demand for long-lasting strategies that enhance moisture management and protect against microbes without unduly compromising the hand or comfort in garment applications.

SUMMARY OF THE INVENTION

The present invention provides strategies to improve the moisture management properties of textiles while retaining high comfort levels. The moisture management properties are demonstrated by data showing that treated fabrics have improved wicking characteristics and stable drying times. The treatments also help to protect textiles against microbial growth. The antimicrobial properties are demonstrated by data showing that treatments according to the present invention provided antimicrobial protection comparable to that provided by a well known, commercially available antimicrobial treatment. The treatments can be used in combination with other moisture management and/or antimicrobial systems if desired.

The treatments are long-lasting and durable. Illustrative embodiments help to manage moisture and provide antimicrobial protection even after treated samples have been washed many times (e.g., 10 washing cycles).

The treatment strategies of the present invention are based at least in part on the use of cationic bis-imidazoline(s) and their salts. Quaternized bis-imidazoline cations and their salts are particularly preferred. Without wishing to be bound, it is believed that the multiple imidazoline rings and an excellent balance between hydrophilic and hydrophobic properties help to provide the improved moisture management performance while also showing strong association with the textile so that the improvements are long lasting.

These materials in many modes of practice are derived from amine admixtures comprising linear tetramines optionally in combination with other tetramines and/or other amines. The materials are made efficiently and at high yield using an improved synthesis that involves a combination of low pressure and moderately high temperatures. These conditions avoid the need to use catalyst systems, although catalysts could still be used if desired. The synthesis strategy is robust enough to work with variable composition raw materials and delivers equimolar conversion and quantitative yield of the product in lower reaction times.

In one aspect, the present invention relates to a method of making a quaternized bis-imidazoline, comprising the steps of:

a) providing a bis-amide according to the formula

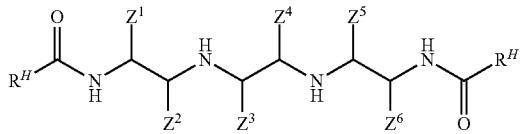

wherein each $Z^1$, $Z^2$, $Z^3$, $Z^4$, $Z^5$, and $Z^6$ independently is a monovalent moiety or a co-member of a ring structure with another $Z^1$, $Z^2$, $Z^3$, $Z^4$, $Z^5$, and $Z^6$;
and each $R^H$ independently is a hydrophobic, monovalent moiety comprising 6 to 50 carbon atoms;

b) causing ingredients comprising at least the bis-amide to form a bis-imidazoline according to the formula

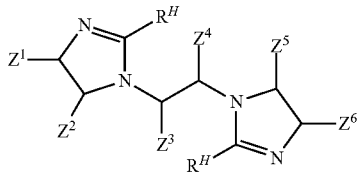

wherein at least a portion of forming the bis-imidazoline occurs in a vacuum at a temperature less than 325° C.; and c) using ingredients comprising the bis-imidazoline to form a quaternary, ammonium cation or salt thereof.

In another aspect, the present invention relates to a method of treating a fabric, comprising the steps of:

a) providing a fabric;
b) causing at least a portion of the fabric to contact a composition comprising a quaternary ammonium bis-imidazoline cation or salt thereof, said cation or salt being derived from one or more ingredients comprising at least a bis-imidazoline having the formula

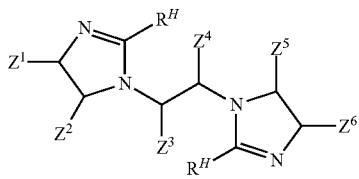

wherein each $Z^1$, $Z^2$, $Z^3$, $Z^4$, $Z^5$, and $Z^6$ independently is a monovalent moiety or a co-member of a ring structure with another $Z^1$, $Z^2$, $Z^3$, $Z^4$, $Z^5$, and $Z^6$; and each $R^H$ independently is a hydrophobic, monovalent moiety comprising 6 to 50 carbon atoms.

In another aspect, the present invention relates to a method of making a garment; comprising the steps of:

a) providing a fabric, wherein the fabric or a component thereof has been contacted with a composition comprising a quaternary ammonium bis-imidazoline cation or salt thereof, said cation or salt being derived from one or more ingredients comprising at least a bis-imidazoline having the formula

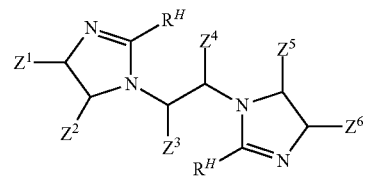

wherein each $Z^1$, $Z^2$, $Z^3$, $Z^5$, and $Z^6$ independently is a monovalent moiety or a co-member of a ring structure with another $Z^1$, $Z^2$, $Z^3$, $Z^4$, $Z^5$, and $Z^6$; and each $R^H$ independently is a hydrophobic, monovalent moiety comprising 6 to 50 carbon atoms; and b) using the fabric to make the garment.

In another aspect, the present invention relates to a method of making a treated fabric comprising the steps of:

a) providing a polymer;
b) causing at least a portion of the polymer to contact a composition comprising a quaternary bis-imidazoline cation or salt thereof, said cation or salt being derived from one or more ingredients comprising at least a bis-imidazoline having the formula

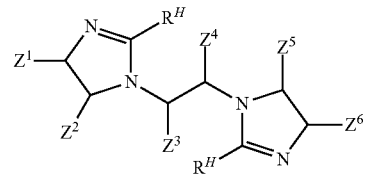

wherein each $Z^1$, $Z^2$, $Z^3$, $Z^4$, $Z^5$, and e independently is a monovalent moiety or a co-member of a ring structure with another $Z^1$, $Z^2$, $Z^3$, $Z^4$, $Z^5$, and $Z^6$;
and each $R^H$ independently is a hydrophobic, monovalent moiety comprising 6 to 50 carbon atoms; and c) incorporating the polymer into a fabric.

In another aspect, the present invention relates to a treated garment, comprising a treated fabric prepared by contacting at least a portion of the treated fabric with a composition comprising a quaternary bis-imidazoline cation or salt thereof, said cation or salt being derived from one or more ingredients comprising at least a bis-imidazoline having the formula

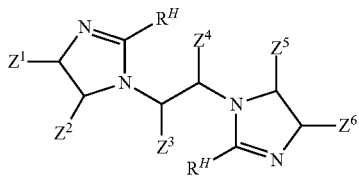

wherein each $Z^1$, $Z^2$, $Z^3$, $Z^4$, $Z^5$, and $Z^6$ independently is a monovalent moiety or a co-member of a ring structure with another $Z^1$, $Z^2$, $Z^3$, $Z^4$, $Z^5$, and $Z^6$;

and each $R^H$ independently is a hydrophobic, monovalent moiety comprising 6 to 50 carbon atoms.

BRIEF DESCRIPTION OF THE DRAWINGS

FIG. 1 schematically shows how a bis-imidazoline compound is prepared from linear triethylenetetramine (L-TETA) and oleic acid.

DETAILED DESCRIPTION OF PRESENTLY PREFERRED EMBODIMENTS

The embodiments of the present invention described below are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

In one aspect, the present invention involves the preparation of cationic bis-imidazolines and salts thereof that are useful in textile treatments, particularly treatments for fabrics used to make garments (e.g., clothing, head gear, hand gear, etc.). The treatments help manage moisture and/or to protect against microbes. Without wishing to be bound, it is also believed that the treatments could help to provide textiles with antistatic properties and also could further protect textiles via some degree of fungicide, bactericide, and/or moldicide properties. Quaternary bis-imidazoline cations and salts thereof are particularly useful in the practice of the present invention.

Quaternized bis-imidazoline cations and their salts useful in the practice of the present invention are derived from one or more bis-imidazoline compounds according to Formula I:

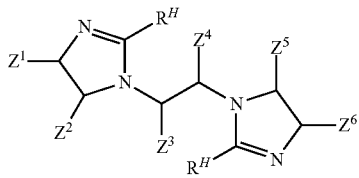

wherein each $Z^1$, $Z^2$, $Z^3$, $Z^4$, $Z^5$, and $Z^6$ independently is a monovalent moiety such as H; a hydrocarbyl of 1 to 10, preferably 1 to 4, and most preferably 1 to 2 carbon atoms; and/or two of the $Z^1$, $Z^2$, $Z^3$, $Z^4$, $Z^5$, and $Z^6$ moieties are linked to each other in a manner effective to form a divalent moiety, such as a hydrocarbylene moiety, that attaches to the corresponding imidazoline ring(s) at two attachment sites. In many embodiments, each $Z^1$, $Z^2$, $Z^3$, $Z^4$, $Z^5$, and $Z^6$ is independently H, methyl, and/or ethyl. A hydrocarbylene moiety is a divalent, saturated hydrocarbon such as —$CH_2$—; —$CH_2CH_2$; —$CH_2CH_2CH_2$—; —$CH_2CH_2CH_2$ $CH_2$—; —$CH_2CH(CH_3)CH_2CH_2$—; —$CH_2C(CH_3)_2CH_2$ $CH_2$—; —$CH_2CH(CH_3)$ $CH(CH_3)CH_2$—; —$CH_2CH(CH_3)$ $CH_2$—; —$CH(CH_3)CH_2CH_2$—; or the like.

Each $R^H$ independently is a hydrophobic, aliphatic, monovalent moiety comprising 6 to 50, preferably 8 to 30, more preferably 10 to 20 carbon atoms. $R^H$ may be linear, branched or cyclic. $R^H$ may be saturated or unsaturated. Optionally, $R^H$ may include one or more heteroatoms such as O, P, S, N, or the like so long as the heteroatom content is limited so that the $R^H$ moiety is hydrophobic. As used with respect to each $R^H$ moiety, the term hydrophobic means that other than carbon and hydrogen, the moiety includes no more than one other type of atom per every 6 or more, preferably every 8 or more, more preferably every 10 or more carbon atoms. For example, monovalent moieties according to Formula A and Formula B:

Formula A

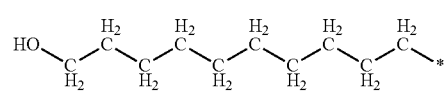

Formula B

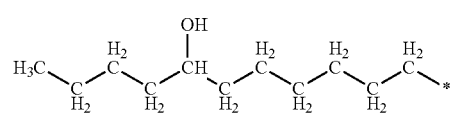

are hydrophobic. Formula A includes 10 carbon atoms per oxygen atom (10:1 ratio). Formula B includes 11 carbon atoms per oxygen atom (11:1 ratio).

In contrast, monovalent moieties according to Formula C and Formula D

Formula C

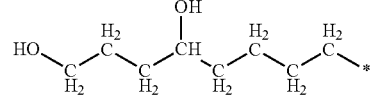

Formula D

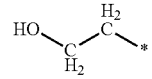

are not hydrophobic. Formula C includes 4 carbon atoms per oxygen atom (4:1 ratio). Formula D includes 2 carbon atoms per one oxygen atom (2:1 ratio).

Unsaturated embodiments of $R^H$ are useful in some embodiments, as corresponding $R^H$ sources (e.g., fatty acids as discussed below) as well as resultant bis-imidazolines may tend to be liquids at room temperature. Exemplary unsaturated embodiments of $R^H$ include one or more of the cis and/or trans versions of one or more of the following:

$CH_3(CH_2)_3CH=CH(CH_2)_7$—

$CH_3(CH_2)_5CH=CH(CH_2)_7$—

$CH_3(CH_2)_8CH=CH(CH_2)_4$—

$CH_3(CH_2)_7CH=CH(CH_2)_7$—

$CH_3(CH_2)_7CH=CH(CH_2)_7$—

$CH_3(CH_2)_5CH=CH(CH_2)_9$—

CH₃(CH₂)₄CH=CHCH₂CH=CH(CH₂)₇—

CH₃(CH₂)₄CH=CHCH₂CH=CH(CH₂)₇—

CH₃CH₂CH=CHCH₂CH=CHCH₂CH=CH(CH₂)₇—

CH₃(CH₂)₄CH=CHCH₂CH=CHCH₂CH=CHCH₂CH=CH(CH₂)₃—

CH₃CH₂CH=CHCH₂CH=CHCH₂CH=CHCH₂CH=CHCH₂CH=CH(CH₂)₃—CH₃(CH₂)₇CH=CH(CH₂)₁₁—

CH₃CH₂CH=CHCH₂CH=CHCH₂CH=CHCH₂CH=CHCH₂CH=CHCH₂CH=CH(CH₂)₂—

Saturated embodiments of $R^H$ also may be useful. Exemplary saturated embodiments of $R^H$ include one or more of

CH₃(CH₂)₆—

CH₃(CH₂)₈—

CH₃(CH₂)₁₀—

CH₃(CH₂)₁₂—

CH₃(CH₂)₁₄—

CH₃(CH₂)₁₆—

CH₃(CH₂)₁₈—

CH₃(CH₂)₂₀—

CH₃(CH₂)₂₂—

CH₃(CH₂)₂₄—

Exemplary embodiments of $R^H$ including one or more heteroatoms may include pendant hydroxyl functionality. An example of this kind of $R^H$ moiety is a monounsaturated hydrocarbon chain of 17 carbon atoms (with the first carbon of the chain being attached to the nitrogen of the imidazoline ring in Formula I above or IA below) that includes an OH pendant from the 12$^{th}$ carbon atom of the chain and that includes a double bond between the 8$^{th}$ and 9$^{th}$ carbons.

Each of the $R^H$ embodiments described above may be sourced from the corresponding fatty acid(s) according to the formula $R^H$—COOM, defined below. Schematically, the $R^H$ moiety can be viewed as the "tail" of the fatty acid. The fatty acids may be used to prepare the bis-imidazoline(s) according to the synthesis schemes described below. In such schemes, the carbon of the COOH group becomes part of an imidazoline ring, and the tail portion becomes an $R^H$ substituent of the ring according to Formula I.

An exemplary compound according to Formula I has the structure shown in Formula IA:

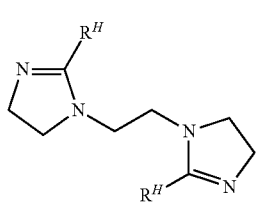

In a preferred embodiment of a compound according to Formula IA, $R^H$ has the cis and/or trans, preferably cis, structure as follows:

—(CH₂)₇C=C(CH₂)₇CH₃

In many modes of practice, one or more bis-imidazoline cations and salts thereof are obtained by quaternizing one or more bis-imidazoline compounds according to Formula I According to Formula I, the bis-imidazoline includes four nitrogens, wherein two nitrogens are associated with each of the imidazoline rings, respectively. In each ring, one of the nitrogens is a tertiary nitrogen while the other is an imine nitrogen. Without wishing to be bound by theory, it is believed that, on average, at least one and possibly both tertiary nitrogens are quaternized. Without wishing to be bound by theory, it also is believed that in some embodiments, the positive charge resulting from quaternization of an imidazoline ring could resonate between the tertiary amine nitrogen and the imine nitrogen. As used herein, an imine nitrogen is a nitrogen that forms a double bond with a carbon atom.

A quaternized bis-imidazoline cation in which one tertiary nitrogen is quaternized may be represented by the following structure according to Formula IB-1:

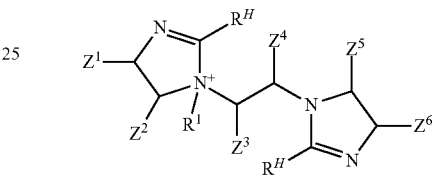

wherein each $Z^1$, $Z^2$, $Z^3$, $Z^4$, $Z^5$, and $Z^6$ is as defined above, each $R^H$ is as defined above, and $R^1$ is a monovalent moiety other than H. In many embodiments, $R^1$ may be aromatic or aliphatic. Aliphatic embodiments are presently preferred. $R^1$ may be linear, branched or cyclic. $R^1$ may be saturated or unsaturated. Preferably, $R^1$ is saturated. Optionally, $R^1$ may include one or more heteroatoms such as O, P, S, N, or the like. Preferably, $R^1$ is a monovalent hydrocarbyl moiety of 1 to 20, preferably 1 to 4, more preferably 1 to 3 carbon atoms. Exemplary hydrocarbyl embodiments of $R^1$ include methyl, ethyl, propyl, isopropyl, butyl, t-butyl, i-butyl, and the like.

In some modes of practice, the positive charge resulting from quaternization of an imidazoline ring could resonate between the tertiary amine nitrogen and the imine nitrogen of that ring. Such a quaternized product may be represented by the structure of Formula IB-2:

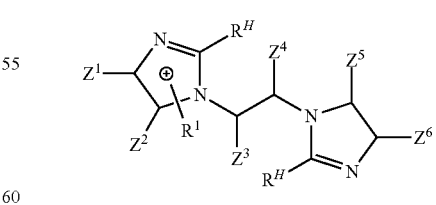

wherein each $Z^1$, $Z^2$, $Z^3$, $Z^4$, $Z^5$, and $Z^6$, each $R^H$, and $R^1$ is as defined above.

A quaternized bis-imidazoline cation in which both tertiary nitrogens are quaternized may be represented by the following structure according to Formula IC-1:

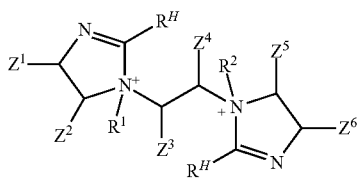

wherein each $Z^1$, $Z^2$, $Z^3$, $Z^4$, $Z^5$, $Z^6$, $R^H$, and $R^1$ is as defined above; and $R^2$ independently may be a monovalent moiety having the same definition as $R^1$, although $R^1$ and $R^2$ need not be the same.

In some modes of practice, the positive charges resulting from quaternization of the two imidazoline rings could resonate on each ring between the tertiary amine nitrogen and the imine nitrogen of that ring. Such a quaternized product may be represented by the structure of Formula IC-2:

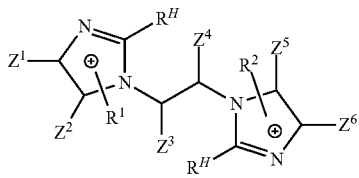

wherein each $Z^1$, $Z^2$, $Z^3$, $Z^4$, $Z^5$, and $Z^6$, each $R^H$, $R^1$, and $R^2$ is as defined above.

In some modes of practice a quaternized bis-imidazolines may comprise a mixture of compounds according to Formulae IB-1, IB-2, IC-1, and/or IC-2. In such mixtures, it is believed that compounds according to Formula IC-1 would be the predominant species with the others being present in lesser amounts. Accordingly, illustrative embodiments of such mixtures may independently comprise 1 to 1000, even 1 to 100, or even 1 to 10 parts by weight of one or more of compounds according to Formulae IB-1, IB-2, and/or IC-2 per 1 to 1000, even 1 to 100, or even 1 to 10 parts by weight of compound(s) according to Formula IC-1.

Salts of the quaternized cation(s) generally incorporate a neutraling amount of one or more anions, wherein such anions are also denoted herein by the symbol $X^-$. Exemplary anions include halide such as $I^-$, $Cl^-$ or $F^-$; sulfate, aryl sulfate, alkyl sulfate, sulfonate, aryl sulfonate, alkyl sulfonate, phosphonate, aryl phosphonate, alkyl phosphonate, phosphate, aryl phosphate, alkyl phosphate, sulfide, arsenate, hydrogen phosphate, dihydrogen phosphate, nitrate, nitrite, hydrogen sulfate, thiosulfate, perchlorate, iodate, chlorate, bromate, chlorite, hypochlorite, hypobromite, carbonate, chromate, hydrogen carbonate, dichromate, acetate, formate, amide, cyanide, cyanate, peroxide, thiocyanate, oxalate, hydroxide, permanganate, combinations, of these, and the like For example, one suitable anion is $R^3OSO_3^-$, wherein $R^3$ is a monovalent moiety, often an aryl or aliphatic monovalent moiety such as phenyl or substituted phenyl, tolyl, or a hydrocarbyl such as methyl, ethyl, propyl, isopropyl, butyl, t-butyl, i-butyl, hexyl, combinations of these, and the like.

Exemplary salts of quaternized bis-imidazoline cations and such anions ($X^-$) may be represented by Formula ID:

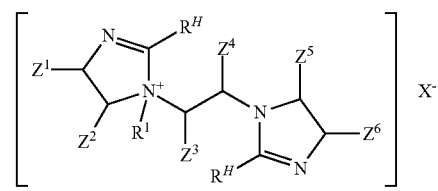

Formula IE:

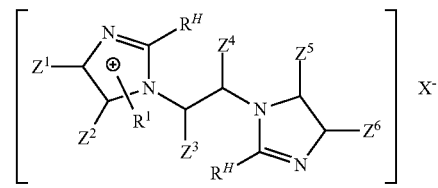

Formula IF:

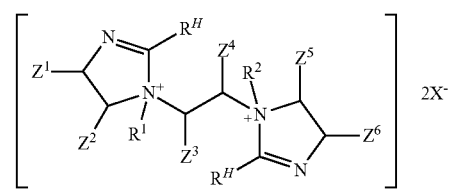

and Formula IG:

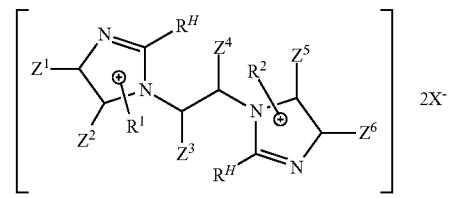

wherein each $Z^1$, $Z^2$, $Z^3$, $Z^4$, $Z^5$, $Z^6$, each $R^H$, $R^1$, $R^2$, and $X^-$ is as defined above.

The present invention provides an advantageous method for preparing quaternized bis-imidazoline salts that optionally may be practiced without using catalyst, activator, and/or solvent. In a first step, one or more amine admixtures comprising one or more linear tetramines according to Formula II (see below) are provided:

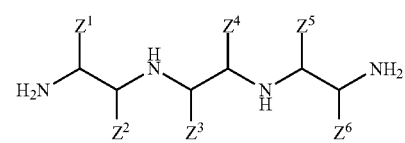

wherein each $Z^1$, $Z^2$, $Z^3$, $Z^4$, $Z^5$, and $Z^6$ independently is as defined above. In an exemplary embodiment, the linear, aliphatic tetramine according to Formula II is linear triethylenetetramine (L-TETA) according to Formula IIA:

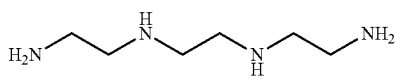

Note that a tetramine according to Formula II has first and second primary amine moieties and first and second secondary amine moieties. Additionally, each primary amine is spaced apart from a corresponding secondary amine by a carbon backbone including 2 carbon atoms. This structure facilitates ring formation as described below. Optionally, the amine admixtures useful in the practice of the present invention optionally may include one or more other tetramines. As used herein, a tetramine is any compound including four amine groups. Often, the tetramine reactants are provided as an admixture comprising a plurality of different tetramines as well as other kinds of amines. The amine groups in the tetramines and other amines may be primary, secondary, and/or tertiary subject to the proviso that the admixture includes one or more linear tetramines according to Formula II.

The amine admixture(s) are used as reactant(s) to first synthesize one or more bis-imidazolines. The bis-imidazolines are then quaternized. This reaction scheme is described in more detail below.

One or more of the provided tetramine(s) may be liquid at room temperature. For example, L-TETA (linear N,N'-bis (2-aminoethyl)-1,2-ethanediamine, also known as linear triethylenetetramine) is a liquid at room temperature. In addition to serving as a tetramine reactant, such a liquid tetramine also may function as a solvent for the reaction, reducing or even eliminating the need for other solvents.

The amount of linear tetramine(s) of Formula II included in an amine admixture may vary over a wide range. For example, an amine admixture may include from 0.1 to 100 weight percent, preferably 20 to 100 weight percent, more preferably 50 to 100 weight percent of one or more linear tetramines according to Formula II based on the total weight of amines included in the admixture. In the practice of the present invention, it is optional to use a tetramine admixture that is prepared or processed to include one or more linear tetramines according to Formula II in relatively pure form. For example, in some modes of practice, at least 75% by weight, preferably at least 85% by weight, more preferably at least 95% by weight, and even more preferably at least 99% by weight of the amines included in the admixture includes one or more linear, aliphatic tetramines according to Formula II.

Amine admixtures including at least 70% by weight, preferably at least 85% by weight, more preferably at least 95% by weight, and even more preferably at least 99% by weight of the linear, aliphatic tetramine(s) according to Formula II are referred to herein as being enriched. Using enriched amine admixtures is optional. The enriched tetramine(s) may be obtained from one or more source(s). As one option, an enriched tetramine product may be obtained from a commercial source and then purified or otherwise processed to provide an admixture that is enriched with respect to linear tetramine(s). For example, one source is commercially available from The Dow Chemical Co. under the trade designation Amine Multi-Use Emulsifier. This product generally contains 65 weight percent or less of linear tetramines but can be purified or otherwise processed to become enriched. This product also may be used as supplied as a suitable amine admixture without enrichment, inasmuch as using enriched amine admixtures is optional.

As used herein, a tetramine admixture that has less than an enriched content with respect to linear tetramine according to Formula II will be referred to as being "lean." Techniques for refining lean tetramine sources to produce enriched tetramine material have been described in U.S. Pat. Pub. No. 2013/0204044.

Enriched tetramines also may be manufactured using a variety of different techniques. As one manufacturing option, ethylene dichloride (EDC) may be used to form a product admixture that often is a mixture of amines in which linear tetramines according to Formula II constitute no more than about 65 weight percent of the tetramine content. Accordingly, the lean product mixture obtained from EDC-based processes typically is further refined in order to obtain enriched tetramine material useful in the practice of the present invention. EDC techniques have been described in U.S. Pat. Pub. No. 2013/0204044.

Another useful option for providing enriched tetramine material involves using transamination techniques to form a product admixture that often is a mixture of amines in which linear tetramines according to Formula II constitute more than about 65 weight percent of the tetramine content. An advantage of using transamination techniques is that transamination may directly provide an enriched tetramine product that is useful in the practice of the present invention. In some modes of practice, transamination provides an enriched tetramine material, but techniques such as those described in U.S. Pat. Pub. No. 2013/0204044 can be practiced to enrich the material even further with respect to linear tetramine content. Transamination techniques useful to form enriched, linear tetramine have been described in U.S. Pat. Pub. No. 2010-0094007-A1, and U.S. Pat. Nos. 8,188,318; 8,293,676 and 8,187,997.

According to another option to provide enriched tetramine composition, U.S. Pat. Pub. No. 2013/0090453 describes a process in which L-TETA is prepared by hydrogenating ethylenediaminediacetonitrile (EDDN) in tetrahydrofuran (THF) in a reactor pressurized with hydrogen. Raney cobalt was used as a catalyst. The product including a mixture of amines including 76.7% TETA.

In addition to including any amount of linear tetramines according to Formula II (including but not limited to embodiments in which the linear tetramine content according to Formula II is enriched), the tetramine(s) provided in the first step optionally may include one or more other linear, branched, or cyclic tetramines. Examples of such other tetramines include one or more of, N,N'-bis-(2-aminoethyl) piperazine (DAEP); N[(2-aminoethyl)2-aminoethyl]piperazine (PEEDA); tris-(2-aminoethyl)amine (TAEA); combinations of these; and the like.

In addition to the tetramines, one or more other amine functional compounds with a greater or lesser number of amine groups than the tetramines can be provided in the first step as well. If present, the weight ratio of tetramine(s) to such other amines may be in the range from 100:0.0001 to 100:50, preferably 100:0.0001 to 100:1. In some modes of practice, these other amines may be monomers, oligomers, and/or polymers. A monomer is a compound including at least one functionality that allows the compound to bond with two or more co-reactive species, that may be the same or different, to form oligomers and polymers. As used herein, an oligomer refers to a compound incorporating two or more monomers (which may be the same or different) and including up to 30 carbon atoms, often 4 to 30 carbon atoms. A polymer refers to a compound incorporating two or more monomers (which may be the same or different) and/or oligomers (which may be the same or different) and including more than 30 carbon atoms. Exemplary amine functional polymers may have a number average weight in the range from 500 to 500,000, sometimes 2000 to 250,000, or sometimes 2000 to 100,000. Gel permeation chromatography (GPC) techniques are useful for determining number average molecular weight in the practice of the present invention.

In a second step, the one or more amine admixtures including one or more linear tetramines according to Formula II are reacted with at least one co-reactive reactant according to Formula III

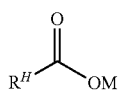

wherein $R^H$ is as defined above and M is any moiety such that the —COOM functionality is co-reactive with a primary amine functionality of the enriched tetramine reactant(s) to form an amide linkage. In many embodiments, M is H, methyl, ethyl, combinations of these or the like. Preferably, M is H. Compounds according to Formula III in which M is H are fatty acids. Accordingly, many useful modes of practice involve reacting one or more linear tetramines according to Formula II with one or more fatty acids according to the formula IIIA

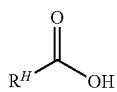

wherein $R^H$ is as defined above.

The reaction between a linear tetramine according to Formula II and a co-reactive reactant according to Formula III forms a bis-amide according to Formula IV

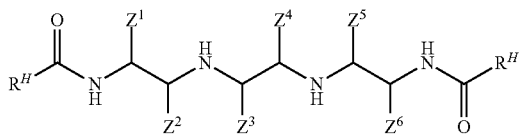

wherein each $R^H$ and each $Z^1$, $Z^2$, $Z^3$, $Z^4$, $Z^5$, and $Z^6$ is independently as defined above. The reaction can occur in a variety of ways. According to one technique, one or more linear tetramines are reacted with a stoichiometric amount of one or more fatty acids (or derivatives of a fatty acid that are co-reactive with the linear tetramine material). The stoichiometric reaction involves two moles of fatty acid (or derivative thereof) reacting with each mole of the tetramine. Although a stoichiometric excess of fatty acid (or derivative thereof) can be used, this is not required or even desirable, as the reaction proceeds to completion without the excess. It is useful to gradually add the tetramine material to the fatty acid (or derivative thereof) rather than to combine the reactants together all at once. This avoids formation of by-products such as amine salt while favoring formation of the bis-amide.

The reaction can occur at a variety of pressures and temperatures for a suitable duration. Suitable temperatures may be in the range from room temperature to about 160° C. One suitable temperature is 150° C. The reaction may occur at ambient pressure, under vacuum, or at elevated pressure. Ambient pressure with good agitation is suitable in many modes of practice. If desired, the reaction may optionally occur in a protected atmosphere, e.g., nitrogen, although this is not required. After all the fatty acid (or derivative) is added to the reaction mixture, the mixture may be held, desirably while being agitated, at one or more reaction temperatures for a sufficient duration to allow the reaction to proceed to a desired degree. In representative modes of practice, this may be from 2 minutes to 48 hours. Maintaining the reaction mixture under the reaction conditions for 4 hours was suitable in one embodiment, for example.

In a third step, the bis-amide according to Formula IV is caused to form a bis-imidazoline according to Formula V

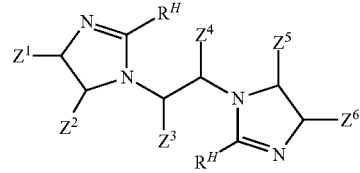

wherein each $R^{11}$ and each $Z^1$, $Z^2$, $Z^3$, $Z^4$, $Z^5$, and $Z^6$ independently is as defined above. Schematically, the imidazoline rings form when the carbon of each —C(O)— moiety in the compound of Formula IV covalently bonds to the corresponding nitrogen at the corresponding "5" position as schematically shown by the dotted lines in the following Formula IVA:

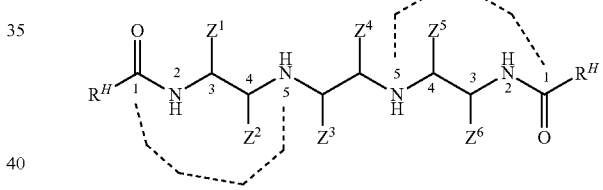

Ring formation causes the resultant structure of Formula V to include a tertiary amine in each imidazoline ring and an imine in each imidazoline ring.

The formation of the bis-imidazoline rings can be accomplished with or without first isolating the bis-amide intermediate. It is convenient in many modes of practice to proceed with ring formation without first isolating the bis-amide. This allows the ring formation to proceed in the same reaction vessel as was used for the formation of the bis-amide.

Ring formation to form the bis-imidazoline can occur under similar conditions regardless of whether the bis-amide is isolated first or not. According to an advantageous technique, ring formation is driven by increasing the temperature of the bis-amide under reduced pressure while removing water by-product to help drive the reaction. Using a combination of elevated temperature and reduced pressure, ring formation occurs even in the absence of catalyst. Suitable temperatures are in the range from 180° C. to 250° C. In one mode of practice, 220° C. was suitable. To help remove water, and thereby to help drive the reaction, the pressure is reduced to any pressure below ambient pressure. In some modes of practice, using a vacuum under 500 mbar (millibar), preferably under 100 mbar, more preferably under 10 mbar, and even more preferably under 1 mbar. The reaction mixture desirably is agitated during at least a portion of the time that the ring formation reaction proceeds.

The ring formation reaction occurs for a sufficient duration to allow the reaction to proceed to a desired degree. In representative modes of practice, this may be from 2 minutes to 48 hours. Maintaining the reaction mixture under the reaction conditions for 5 hours was suitable in one embodiment, for example.

The progress of the ring formation reaction can be monitored using any suitable technique. For example, IR spectroscopy, NMR, and/or liquid chromatography-mass spectrometry (referred to as LCMS or HPLC-MS) can be used to monitor until the amide functionality is reduced to the desired degree. In one mode of practice, the reaction proceeded until no residual amide functionality was detected by LCMS and NMR, indicating substantially complete conversion of the bis-amide to the bis-imidazoline.

Advantageously, no catalyst or solvent is needed to form the bis-amide or bis-imidazoline. Catalysts or solvents could be used if desired, however.

An exemplary reaction scheme 10 to form a bis-imidazoline from L-TETA 12 and oleic acid 14 is shown in FIG. 1. In a first step 100, one mole of L-TETA 12 is reacted with 2 mol of oleic acid 14. The carboxylic acid functionality on the oleic acid 14 reacts with the primary amine functionality on the L-TETA 12 to form a bis-amide intermediate product 16. According to the stoichiometry, two moles of water are produced as a by-product of the amide formation. Next, in reaction step 102, the bis amide product 16 is treated under conditions so that the bis-imidazoline 18 of the present invention is formed. According to the stoichiometry, two moles of water are produced as a by-product of the imidazoline formation.

In a next reaction step, the bis-imidazoline is quaternized under conditions such that one or more of the nitrogens is quaternized. In an illustrative mode of practice, quaternization is achieved by alkylation of at least one of the tertiary amines or at least one of the imines present in one or both of the imidazoline rings. Alkylation generally involves the transfer of an alkyl group from one molecule (here an alkyl source) to another compound (here the bis-imidazoline). Alkylation may be accomplished using one or more alkylating agents. Examples of alkylating agents include alkyl halides such as alkyl iodides; alkyl sulfates such as dimethyl sulfate; sulfonate esters (e.g., mesylate, esylate, tosylate, or besylate, esters), alkyl carbonates, trimethylsilyldiazomethane, dialkyl acetals of N,N-dimethylformamide, lactim ethers of cyclic amides, thiazynes, combinations of these, and the like.

To carry out the quaternization, at least one alkylating agent is gradually added under agitation to the bis-imidazoline. The total amount of alkylating agent added to the bis-imidazoline can vary over a wide range. Generally, the molar ratio of alkylating agent to bis-imidazoline is greater than 1, desirably 1.1:1 to 25:1, more desirably 2:1 to 10:1. In one mode of practice, a molar ratio of 4:1 would be suitable. Using a higher molar ratio of the alkylating agent(s) helps to provide a product with lower viscosity to offer material handling advantages (e.g., transferring, pumping, etc.).

Alkylation can be carried out at any suitable temperature. Heating the reaction medium helps the progress of the reaction. In illustrative modes of practice, the reaction medium may be maintained in the range of 80° C. to 130° C. under reflux hi order to carry out the reaction.

The alkylation reaction may be carried out for any suitable duration. In illustrative modes of practice, the reaction occurs for 5 minutes to 48 hours, desirably 15 minutes to 24 hours, more desirably 1 to 6 hours.

The reaction medium may be used to isolate or otherwise work up the resultant quaternized product. Often, the product is recovered as one or more bis-imidazoline salts.

Additional aspects of the present invention involve textile treatment compositions useful to treat a wide variety of textiles in order to help manage moisture and/or protect against microbes. The treatment compositions advantageously incorporate one or more cationic bis-imidazoline compounds of the present invention, particularly one or more quaternized embodiments thereof.

In many embodiments, treatment compositions of the present invention are aqueous. The aqueous composition can be pre-formed with a desired amount of bis-imidazoline cation, optionally with one or more other components. The premixed composition can then be used to treat a textile to help improve the ability of the textile to manage moisture or to help protect the textile from microbes. In some embodiments, the textile is a textile that is subsequently used to fabricate or is otherwise incorporated into a garment after the treatment. In other embodiments, the treatment can be carried out on an existing garment. As an option, an aqueous composition can be formed as a concentrate and then diluted to prepare a formulation more suitable for substrate treatment. In other aspects, an aqueous composition of the desired dosage may be generated in situ by adding a concentrate or at least one bis-imidazoline cation or salt thereof to water already present in a system.

Nonaqueous treatment compositions also are within the scope of the invention. In these, one or more bis-imidazoline cations of the present invention or salts thereof are incorporated into media in which substantially all of the fluid carrier is an organic solvent such as glycol ethers, alcohols, combinations of these, and the like. Other treatment compositions may include solvents that comprise a combination of water and one or more organic liquids in any other suitable proportion. For example, some embodiments may include from about 0.001 to 100 parts by weight of one or more organic liquids per 1 to 100,000 parts by weight of water.

The amount of one or more bis-imidazoline cations or salts thereof in a treatment composition may be selected within a wide range. In applications where the treatment will be applied using exhaust techniques or padding techniques (see below), treatment compositions desirably include from 0.1 to 100 grams per liter, desirably 1 to 50 grams per liter, more desirably 1 to 20 grams per liter of one or more bis-imidazoline cations or salts thereof based on the total volume of the treatment composition. Concentrates may be formulated more concentrated than this, e.g., 2× to 1000× more concentrated, and then diluted as desired closer to the time of use.

In addition to the bis-imidazoline compound(s), a moisture management additive composition can include one or more other ingredients such as those selected from biocides, polymeric dispersants, scale inhibitors, pH adjusters including buffering agents, surfactants, other corrosion inhibiting agents, fungicides, moldicides, antioxidants, UV inhibitors, coloring agents, taggants, gelling agents, etchants, antiskid agents, anti-foam agents, combinations of these, and/or the like. The quaternized bis-imidazoline compounds of the present invention have surfactant characteristics, making it unnecessary to use additional surfactant material, although one or more additional surfactants could be used if desired.

In many embodiments, a treatment composition of the present invention has an acidic pH. For example, some embodiments may have a pH in the range from 4.0 to 6.9, preferably 5.0 to 6.0. In one mode of practice, formulating a treatment composition at a pH of 5.5 would be suitable. A wide variety of pH adjusters may be used to help formulate at an acidic pH. Examples include organic acids such as acetic acid, citric acid, uric acid, lactic acid, formic acid, oxalic acid, or the like. Inorganic acids also may be used. Acetic acid is preferred. Buffering agents optionally may be used to help stabilize the pH. Examples of suitable buffering agents include sodium acetate, combinations of these, and the like.

The treatment compositions can be used to treat a wide variety of substrates including leather, rugs, carpets, fabrics, thread, garments, tarps, bags, baskets, luggage, bedding, towels, art surfaces, wall coverings, flags, tents, handkerchiefs, balloons, kites, sails, parachutes, brushes, mattresses, sacks, hammocks, awnings, as well as other textiles, fabrics, and cloths, and the like. Substrates can be formed from natural and/or synthetic materials. Substrates may be woven and/or nonwoven. Materials used to make substrates can be sourced from animals, plants, minerals, or synthetic materials. Examples of such materials include hair, fur, skin, silk, grass, rush, hemp, sisal, straw, hay, bamboo, pulpwood, cotton, rice, nettle, flax, jute, modal, pina, seaweed, basalt, glass fiber, metal fiber and foil, polyester, polyaramid, acrylic, polyamide, polyimide, polyurethane, polyolefin, polyacrylonitrile, rubber, carbon, protein, combinations of these, and the like. In exemplary modes of practice, the treatment compositions are used to treat woven or nonwoven substrates comprising cotton or polyester/cotton blends. In the cases where the substrate is a fabric comprising cotton or a polyester/cotton blend, the treatment of the present invention advantageously is applied after dyeing and soaping but before the substrate is formed into the finished article.

After a substrate is provided, the treatment is carried out by causing at least a portion of the substrate to contact the treatment composition. Such contact can be accomplished using a variety of techniques. Examples include brushing, spraying, curtain coating, vapor coating, misting, pouring, spin coating, gravure coating, knife coating, pipetting, immersing, incorporating into fluids flowing or otherwise held in a container, vessel, or pipe, or the like. The compositions can be applied to a substrate a single time or two or more times. The compositions may be applied while the substrate is cooled, at room temperature, or heated. In some modes of practice, the compositions are applied in a protected environment, e.g., a nitrogen atmosphere. The compositions may be applied at ambient pressure, in a vacuum, or at an elevated pressure. Sometimes, the treated substrate is a finished article. In other modes of practice, the treated substrate is used after the treatment to make a finished article, such as a garment or the like.

An exhaust process, commonly used in the textile industry to apply dye, is an exemplary technique for treating substrates with treatment compositions of the present invention. To carry out this technique, a bath comprising the treatment composition is prepared. The treatment may be applied at the same time one or more dyes are applied. As an alternative, the treatment may be applied prior to dyeing. As another alternative, the treatment may be applied in a separate process after dyeing. In some cases, the treatment may be applied at multiple times before, during, and/or after dyeing.

After the bath is provided, the substrate is partially or wholly immersed in the bath as desired. Immersion is carried out at a suitable temperature and time period. In some modes of practice, the treatment may be carried out at a temperature from just above the freezing point of the bath up to the reflux temperature of the bath. More desirably, the treatment occurs at a temperature from about ambient temperature to 90° C., more desirably from 35° C. to 50° C. In one mode of practice, 40° C. would be suitable. The immersion may be carried out for a wide range of time periods. Exemplary immersion periods range from 10 seconds to 48 hours, desirably 3 minutes to 10 hours, more desirably 10 minutes to 2 hours. In one mode of practice, 30 minutes would be suitable for a bath maintained at 40° C. The substrate may be immersed a single time or immersed multiple times. After immersion, the substrate desirably is dried using any suitable technique.

A padding process, commonly used in the textile industry to dye fabric, is another exemplary technique for treating substrates with treatment compositions of the present invention. The padding process is often carried out continuously as the substrate is conveyed through the process at high speeds, e.g., 5 meters/min or more, even 50 meters/min or more, or even 120 meters/min or more. To carry out this technique, a bath comprising the treatment composition is prepared. The treatment may be applied at the same time one or more dyes are applied. As an alternative, the treatment may be applied prior to dyeing. As another alternative, the treatment may be applied in a separate process after dyeing. In some cases, the treatment may be applied at multiple times before, during, and/or after dyeing.

The substrate is conveyed through the bath. The conveyance continues as the fabric is passed between rollers to squeeze out air and force the composition into the substrate. The bath step is often referred to as the dip step. The roller step is often referred to as the nip step. The amount of the fluid retained in the substrate after a dip-nip cycle is known as the % pick up or % expression on a weight basis relative to the dry fabric. Thus, 40% expression means that a dry fabric weighing 100 weight units then weights 140 weight units after the dip-nip cycle. In the practice of the present invention, a wide range of % expression conditions may be practiced. The % expression may be controlled by adjusting the nip pressure. Increased pressure results in less expression, but the penetration is better. In many modes of practicing, carrying out padding for 60% to 90% expression is suitable. In one mode of practice, 70% expression would be suitable. The dip-nip cycle may be repeated one or more times if desired. In continuous processes such as a padding process, drying a moving substrate at 120° C. would be suitable, as one example.

The present invention will now be further described with respect to the following illustrative examples.

Example 1

Synthesis of Bis-Imidazoline Salt (LTBIS)

This example describes preparing a bis-imidazoline salt (also referred to in these examples and the corresponding data as "LTBIS"). Refined oleic acid was taken in a round bottom flask and heated under agitation. Linear triethylenetetramine (L-TETA, >99% purity) in the stoichiometric ratio of 1 mole of L-TETA per 2 moles oleic acid was gradually added to the flask at 150° C. and atmospheric pressure under agitation. The reaction mass was maintained under these conditions for up to 4 hrs to form a bis-amide. The reaction set-up was fitted with a condenser and receiver assembly to recover the water generated (~2 moles/mole of L-TETA) during the bis-amide formation. To convert the bis-amide to a bis-imidazoline, the temperature of the product mixture was increased while also reducing pressure. Specifically, the bis-amide was further maintained at 220° C. under vacuum (preferably <1 mbar) and agitation for up to 5 hrs to drive the imidazoline ring formation step while removing the water by-product (~2 moles/mole of 1-TETA). The reaction completion was confirmed by the analysis (NMR and LCMS) of the mass for no residual amide and complete imidazoline conversion. No catalyst or solvent was used in the reaction scheme to form the bis-amide or the bis-imidazoline.

Next, the bis-imidazoline is quaternized with an alkylating agent. To the bis-imidazoline, dimethyl sulfate (2-4:1 moles/mole of bis-imidazoline) was gradually added under agitation and the reaction mass maintained in the range 80° C. to 130° C. for 3 hrs under reflux. The cationic surfactant (quaternized bis-imidazoline salt) was analyzed and found to have a surface tension of 30-40 mN/m and a critical micellar concentration of 2-8 ppm.

Example 2

Preparation of Treatment Concentrate

The quaternized salt of Example 1 was used to prepare a concentrate. 50 parts by weight of the quaternized salt was dissolved in 50 parts by weight of water. The resultant concentrate thus included 50 weight percent of the active material.

Example 3

Preparation of Recipe 1

The concentrate of Example 2 was combined with sufficient water so that the resultant treatment composition included 10 grams per liter (gpl) of the concentrate.

Example 4

Preparation of Recipe 2

The concentrate of Example 2 was combined with sufficient water so that the resultant treatment composition included 20 grams per liter (gpl) of the concentrate.

Example 5

Rate of Drying on 100% Polyester

A padding process was used to impregnate fabric samples (100% polyester) with Recipe 1, Recipe 2, and a control recipe (water only). The dry weight, padded weight, and weight after drying for 30 minutes, 60 minutes, and 90 minutes are reported in the following Table 5A. All weights are grams. Drying occurred in a closed chamber at room temperature and at a relative humidity of 65%.

|  | Original | | L-TETA based 10 gpl | | L-TETA based 20 gpl | |
| --- | --- | --- | --- | --- | --- | --- |
| Time | 1 | rate | 1 | rate | 1 | rate |
| Initial | 0.895 |  | 0.941 |  | 0.941 |  |
| 5 | 1.719 | 71.9 | 1.858 | 85.8 | 1.858 | 85.8 |
| 15 | 1.488 | 48.8 | 1.343 | 34.3 | 1.343 | 34.3 |
| 30 | 1.218 | 21.8 | 1.019 | 1.9 | 1.019 | 1.9 |

-continued

|  | Original | | L-TETA based 10 gpl | | L-TETA based 20 gpl | |
| --- | --- | --- | --- | --- | --- | --- |
| Time | 1 | rate | 1 | rate | 1 | rate |
| 45 60 |  |  | 0.94 | −6 | 0.94 | −6 |

The data shows that treated polyester fabric have improved drying rates compared to untreated polyester fabric. The moderate improvement in drying rate by increasing dosage from 10 gpl to 20 gpl indicates that 10 gpl is a more optimum and efficient concentration for moisture management in polyester

Example 6

Wicking Rate on 100% Polyester

A padding process was used to impregnate fabric samples (100% polyester) with Recipe 1, Recipe 2, and a control recipe (water only). The samples were padded to provide 70 weight percent expression and then cured at 150° C. for 5 min. This means that a padded fabric included 100 parts by weight of fabric and 70 parts by weight of the impregnating solution.

The wicking rate of the padded fabric samples was evaluated. Wicking involves a capillary action in warp and weft directions. The procedure of ISO 9073 is used. The results are shown in Tables 6A (Control), Table 6B (Recipe 1), and Table 6C (Recipe 2).

TABLE 6A

Wicking rate, Control

| Duration | warp Height (cm) | weft Height (cm) |
| --- | --- | --- |
| 10 sec | 0.63 | 0.6 |
| 30 sec | 0.73 | 0.7 |
| 60 sec | 0.86 | 0.8 |
| 300 sec. | 1.06 | 0.96 |

TABLE 6B

Wicking rate, Recipe 1

| Duration | warp Height (cm) | weft Height (cm) |
| --- | --- | --- |
| 10 sec | 1.86 | 2.13 |
| 30 sec | 2.23 | 3.23 |
| 60 sec | 5.86 | 4 |
| 300 sec. | 7.86 | 7.06 |

TABLE 6C

Wicking rate, Recipe 2

| Duration | warp Height (cm) | weft Height (cm) |
| --- | --- | --- |
| 10 sec | 2.23 | 2.4 |
| 30 sec | 3.03 | 3.16 |
| 60 sec | 3.9 | 3.83 |
| 300 sec. | 6.56 | 6.5 |

Statistical analysis of the wicking rate data shows that Recipe 1 and 2 provided a significant improvement in wicking rate. Polyester is hydrophobic in nature. Polyester resists absorbing water. In Table 6A, untreated polyester fabric showed minimal water absorption. However, when the fabric is treated with Recipe 1 (Table 6B) or Recipe 2 (Table 6C), there is a substantial improvement in water absorption both in the warp and weft direction.

Example 7

Rate of Drying on 100% Cotton

A padding process was used to impregnate fabric samples (100% cotton) with Recipe 1, Recipe 2, and a control recipe (water only). The dry weight, padded weight, and weight after drying for 30 minutes, 60 minutes, and 90 minutes are reported in the following Table 7A. All weights are grams. Drying occurred in a closed chamber at room temperature and at a relative humidity of 65%. The data in the following table shows that untreated and treated cotton samples show comparable drying rates as is expected for a hydrophilic material such as cotton. Rate of drying is more important, therefore, for fabrics that wholly are partially incorporate hydrophobic material(s). Per Example 9 below, treating cotton still helps to provide cotton with antimicrobial protection.

|  | Control Recipe | Recipe 1 | Recipe 2 |
| --- | --- | --- | --- |
| Dry weight | 1.44 | 1.69 | 1.61 |
| Wet padded weight | 2.87 | 3.39 | 3.22 |
| Weight after 30 min | 2.03 | 2.43 | 2.35 |
| Weight after 60 min | 1.54 | 1.83 | 1.66 |
| Weight after 90 min | 1.43 | 1.66 | 1.60 |

Example 8

Wicking Rate on 100% Cotton

A padding process was used to impregnate fabric samples (100% cotton) with Recipe 1, Recipe 2, and a control recipe (water only). The samples were padded to provide 70 weight percent expression and then cured at 150° C. for 5 min.

The wicking rate of the padded fabric samples was evaluated. Wicking involves a capillary action in warp and weft directions. The procedure of ISO 9073 is used. The results are shown in Tables 6A (Control), Table 6B (Recipe 1), and Table 6C (Recipe 2).

TABLE 8A

Wicking rate, Control

| Duration | warp Height (cm) | weft Height (cm) |
| --- | --- | --- |
| 10 sec | 2.1 | 1.8 |
| 30 sec | 3.07 | 2.4 |
| 60 sec | 3.8 | 3 |
| 300 sec. | 6.5 | 4.7 |

TABLE 8B

Wicking rate, Recipe 1

| Duration | warp Height (cm) | weft Height (cm) |
| --- | --- | --- |
| 10 sec | 2.37 | 2.1 |
| 30 sec | 3.03 | 2.7 |
| 60 sec | 3.4 | 3.2 |
| 300 sec. | 6.5 | 5.6 |

TABLE 8C

Wicking rate, Recipe 2

| Duration | warp Height (cm) | weft Height (cm) |
| --- | --- | --- |
| 10 sec | 1.63 | 1.4 |
| 30 sec | 2.43 | 2.3 |
| 60 sec | 3 | 2.7 |
| 300 sec. | 5.83 | 4.5 |

Statistical analysis of the wicking rate data shows that Recipe 1 and 2 provided a significant improvement in wicking rate. Cotton is hydrophilic in nature and readily absorbs water. In Table 8A, untreated cotton shows significant water absorption. When the fabric is treated with Recipe 1 (Table 8B) and Recipe 2 (Table 8C), water absorption is maintained in both the warp and weft directions. The treatment maintains the hydrophilic nature of cotton.

Example 9

Antibacterial Activity

Recipe 3 was prepared by combining the concentrate of Example 2 with sufficient water so that the resultant treatment composition included 30 grams per liter (gpl) of the concentrate.

A comparison sample (Comparison Recipe 4) was prepared by combining Silvadur AQ antimicrobial composition with sufficient water so that the resultant treatment composition included 10.5 grams per liter of the additive.

Recipe 5 was prepared by combining the concentrate of Example 2 and the Silvadur AQ antimicrobial composition with sufficient water so that the resultant treatment composition included 30 gpl of the concentrate and 10.5 gpl of the Silvadur AQ antimicrobial composition.

Each of Recipe 3, Comparison Recipe 4, and Recipe 5 was applied onto a corresponding 100% cotton substrate by padding to provide treated samples 3A, Comparison 4A, and 5A, respectively. Each of Recipe 3, Comparison Recipe 4, and Recipe 5 was applied onto a corresponding cotton/polyester blend substrate by padding to provide treated samples 3B, Comparison 4B, and 5B, respectively. This is summarized in the following Table 9A:

| No. | Treated with | A, Cotton samples | B, Cotton/Polyester samples |
| --- | --- | --- | --- |
| 3 | Recipe 3 at 30 gpl | 3A | 3B |
| Comparison 4 | Silvadur AQ at 10.5 gpl | 4A | 4B |
| 5 | Recipe 3 at 30 gpl + Silvadur AQ at 10.5 gpl | 5A | 5B |

The antibacterial activity of the treated samples was evaluated using ASTM 2149. The results are shown in the following Table 9B:

| Antibacterial Activity ASTM 2149 | | | |
| --- | --- | --- | --- |
| Original fabric samples | | Test Organisms | % reduction |
| Sample 3A | Quantitative | Escherichia coli (ATCC 11775) | 66% |
| Sample 3B | Quantitative | Escherichia coli (ATCC 11775) | >99% |
| Sample 4A | Quantitative | Escherichia coli (ATCC 11775) | 92% |
| Sample 4B | Quantitative | Escherichia coli (ATCC 11775) | >99% |

-continued

Antibacterial Activity ASTM 2149

| Original fabric samples | Test Organisms | % reduction |
|---|---|---|
| Sample 5A | Quantitative | *Escherichia coli* (ATCC 11775) | 89% |
| Sample 5B | Quantitative | *Escherichia coli* (ATCC 11775) | >99% |

The test results indicated that after one hour, greater than 99.9% antibacterial activity performance was observed for sample 3B, sample 4B, and sample 5B. Sample 4A provided about 92% reduction and sample 5A provided 89.5% reduction after one hour.

The experiment shows firstly that the compositions of the present invention at a reasonable dosage provides antimicrobial action that is comparable to a well known, commercially available Silvadur AQ anti-microbial composition. The experiment further shows that there is no drop in performance of the Silvadur AQ composition when diluted with the compositions of the present invention. In fact, data is observed to show that the combination provides a synergistic improvement in performance.

Example 10

Water Absorbency and Drying Time

Water absorbency and drying time were evaluated using the ADIDAS test protocols. These are an industry standard and are very stringent for determining moisture management. To prepare samples, 100% cotton and 100% polyester is padded with Recipe 1 at 70% expression and then cured at 150° C. for 5 minutes. The fabric was then tested for water absorbency and drying time using the ADIDAS test protocols. The results are shown in the following tables.

TABLE 10A

Water absorbency (6.04) {Adidas requirement} 100% cotton

| | Time | Requirement |
|---|---|---|
| Original | 1 sec | <=2 sec |
| After 5 washes | 1 sec | <=2 sec |
| After 10 washes | 1 sec | <=2 sec |

TABLE 10B

Water absorbency (6.04) {Adidas requirement} 100% Polyester

| | Time | Requirement |
|---|---|---|
| Original | 1 sec | <=5 sec |
| After 5 washes | 1 sec | <=5 sec |
| After 10 washes | 1 sec | <=5 sec |

Drying Time(6.07) {Adidas requirement}

| | Amount of water in gm | |
|---|---|---|
| Original | 0 gm | After 30 min reaching a weight of 0 gm |
| After 5 washes | 0 gm | |
| After 10 washes | 0 gm | |

The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of making a treatment composition comprising a quaternized bis-imidazoline, comprising the steps of:
   a) providing a bis-amide according to the formula wherein each $Z^1$, $Z^2$, $Z^3$, $Z^4$, $Z^5$, and $Z^6$ independently is a monovalent moiety or at least first and second of the $Z^1$, $Z^2$, $Z^3$, $Z^4$, $Z^5$, and $Z^6$ moieties are linked to each other in a manner effective to form a divalent moiety that attaches to the corresponding imidazoline ring(s) at two attachment sites; and each $R^H$ independently is a hydrophobic, monovalent moiety comprising 6 to 50 carbon atoms;
   b) causing ingredients comprising at least the bis-amide to form a bis-imidazoline according to the formula wherein at least a portion of forming the bis-imidazoline occurs in a vacuum at a temperature less than 325° C.; and
   c) using ingredients comprising the bis-imidazoline to form a composition having a pH in the range from 4.0 to 6.9 and comprising a quaternary ammonium bis-imidazoline cation or salt thereof.

2. The method of claim 1, wherein step (b) occurs at a temperature in the range from 180° C. to 250° C. at a pressure below ambient temperature.

3. The method of claim 1, wherein step (b) occurs at a temperature in the range from 180° C. to 250° C. at a pressure below 500 millibar.

4. The method of claim 1, wherein step (b) occurs at a temperature in the range from 180° C. to 250° C. at a pressure below 100 millibar.

5. The method of claim 1, wherein step (b) occurs in the absence of a catalyst.

6. The method of claim 1, wherein step (c) comprises reacting the bis-imidazoline with an alkylating agent.

7. The method of claim 1, wherein the composition has a pH in the range of 5.0 to 6.0.

8. The method of claim 1, wherein the composition comprises an organic acid selected from the group consisting of acetic acid, citric acid, uric acid, lactic acid, formic acid, and oxalic acid.

* * * * *